(12) United States Patent
Baer et al.

(10) Patent No.: US 7,315,364 B2
(45) Date of Patent: Jan. 1, 2008

(54) SYSTEM FOR INSPECTING A SURFACE EMPLOYING CONFIGURABLE MULTI ANGLE ILLUMINATION MODES

(75) Inventors: Adam Baer, Rehovot (IL); Boris Golberg, Ashdod (IL)

(73) Assignee: Applied Materials, Israel, Ltd., Rehovot (IL)

( * ) Notice: Subject to any disclaimer, the term of this patent is extended or adjusted under 35 U.S.C. 154(b) by 110 days.

(21) Appl. No.: 11/123,454

(22) Filed: May 5, 2005

(65) Prior Publication Data

US 2006/0087648 A1    Apr. 27, 2006

Related U.S. Application Data

(60) Provisional application No. 60/622,208, filed on Oct. 25, 2004.

(51) Int. Cl.
G01N 21/00    (2006.01)
(52) U.S. Cl. .............................. 356/237.2; 356/237.3; 356/237.4; 356/237.5
(58) Field of Classification Search ............. 356/237.2, 356/600, 73, 517, 512, 237.1–237.6; 250/234–236, 250/559.04, 559.41, 559.45; 359/201–202
See application file for complete search history.

(56) References Cited

U.S. PATENT DOCUMENTS

| | | | |
|---|---|---|---|
| 5,517,349 A | 5/1996 | Sandstrom | |
| 6,124,924 A | 9/2000 | Feldman et al. | |
| 6,797,975 B2 | 9/2004 | Nishiyama et al. | |
| 6,853,446 B1 | 2/2005 | Almogy et al. | |
| 6,856,384 B1 * | 2/2005 | Rovira | 356/73 |
| 2003/0001120 A1 | 1/2003 | Nishiyama et al. | |
| 2004/0150820 A1 * | 8/2004 | Nikoonahad et al. | 356/364 |
| 2004/0263834 A1 | 12/2004 | Alumot et al. | |

OTHER PUBLICATIONS

Baer, Adam et al., Tilted Illumination Mode, U.S. Appl. No. 60/622,208 filed Oct. 25, 2004 5pp.

* cited by examiner

*Primary Examiner*—Layla G. Lauchman
*Assistant Examiner*—Tri Ton
(74) *Attorney, Agent, or Firm*—Tarek N. Fahmi

(57) ABSTRACT

Apparatus for inspection of a surface, the apparatus including an objective having central and peripheral regions, which is positioned to focus an input beam through the central region in a normal direction onto the surface. The apparatus further includes a first periscope which is positionable to divert the input beam so as to pass through the peripheral region of the objective, whereby the objective focuses the input beam in an oblique direction onto the surface. There is also a second periscope which is positionable to capture radiation reflected from the surface in the oblique direction after passage of the reflected radiation through the peripheral region of the objective.

12 Claims, 3 Drawing Sheets

SYSTEM FOR INSPECTING A SURFACE EMPLOYING CONFIGURABLE MULTI ANGLE ILLUMINATION MODES

CROSS-REFERENCE TO RELATED APPLICATION

This application claims the benefit of U.S. Provisional Patent Application 60/622,208, filed 25 Oct. 2004, which is incorporated herein by reference.

FIELD OF THE INVENTION

The present invention relates generally to defect inspection devices, and specifically to defect inspection devices using radiation that is incident at more than one angle.

BACKGROUND OF THE INVENTION

Detecting defects on the surface of wafers produced in the semi-conducting industry is a critical part of the whole production process. In one type of inspection process for such defect detection, a light beam is focused at a normal angle onto the surface, and the normal reflection from the surface is used to determine the presence of a defect. In some inspection processes, it is advantageous to inspect the surface using light that is incident at an oblique angle to the surface, and to detect the light at the oblique angle.

U.S. Patent Application 2004/0263834 to Alumot et al., whose disclosure is incorporated herein by reference, describes a method and apparatus for inspecting a surface for defects by first inspecting the surface at a high speed low resolution. Suspect areas are then inspected at a low speed high resolution. Inspections may be performed by illuminating the surface normally, and measuring returning light at an oblique angle.

U.S. Patent Application 2003/0001120 and U.S. Pat. No. 6,797,975, both to Nishiyama et al., whose disclosures are incorporated herein by reference, describe apparatus for inspecting a semiconductor device for defects. The apparatus includes an oblique illumination system, and a detector unit that receives returning light at a normal angle. The apparatus also includes auto-focus illumination and receiver units which are aligned obliquely to a surface of the device.

U.S. Pat. No. 6,856,384 to Rovira, whose disclosure is incorporated herein by reference, describes a metrology tool for measuring step heights of a sample on a surface. The tool may use normal and oblique illumination and detection of returning light, and may incorporate an auto-focus mechanism.

U.S. Pat. No. 6,853,446 to Almogy et al., whose disclosure is incorporated herein by reference, describes a variable angle inspection system. A scanning light beam may illuminate a surface at a first angle, and a deflection element may be selectively inserted into a path of the scanning beam so that the beam illuminates the surface at a second angle.

The light inspecting the wafer surface is typically maintained in focus at the surface by an auto-focus mechanism, many of which are known in the art. One such mechanism is described in U.S. Pat. No. 6,124,924 to Feldman et al., whose disclosure is incorporated herein by reference. The disclosure uses the property that in-focus light returns from a region whereon the light is focused in the form of a generally plane wave front. In contrast, out-of-focus light returns from the region in the form of a generally spherical wave front. The disclosure describes a double slit system which is configured so that when the region is in focus images of the slits align, whereas when the region is out of focus the images are misaligned.

SUMMARY OF THE INVENTION

In embodiments of the present invention, apparatus for inspection of a surface comprises an objective component and first and second periscopes. The objective component, typically an objective lens, has central and peripheral regions, and is positioned so that it focuses an input radiation beam through its central region onto the surface, so that the input radiation beam strikes the surface in a normal direction. The first periscope is movable to a first position where it diverts the input beam to pass through the peripheral region of the objective component, so that the component focuses the input beam to strike the surface in an oblique direction. The second periscope, typically fixedly coupled to the first periscope, is movable to a second position where it captures reflected radiation travelling in the oblique direction from the surface, after the reflected radiation has passed through the peripheral region of the objective. The two movable periscopes allow the apparatus to irradiate the surface normally or obliquely via the same objective component.

Typically, the second periscope diverts the reflected radiation along a return path which is substantially parallel to and contiguous with an incoming path of the input beam prior to its diversion by the first periscope. In this case, the apparatus may advantageously be incorporated into an inspection system which operates in one of two modes. In a first mode the periscopes are positioned so as not to interact with the input radiation beam or the reflected radiation, the input radiation beam is directed via the central region of the objective component so as to strike a location on the surface normally, and the reflected radiation traverses substantially the same incoming path as the input beam. In a second mode the periscopes are positioned in their respective positions, so as to direct the input radiation beam to the location at an oblique angle to the surface, and so that the reflected radiation traverses the contiguous parallel return path described above.

In each mode the reflected radiation may be advantageously used for auto-focusing and for detection of a characteristic, such as the presence of an impurity at the location or of a defect of the location. Furthermore, since in both modes the input beam and the reflected radiation follow generally the same paths, there is substantially no requirement to change configurations of detection and/or auto-focus optics comprised in the inspection system when switching modes.

The present invention will be more fully understood from the following detailed description of the embodiments thereof, taken together with the drawings, a brief description of which follows.

DETAILED DESCRIPTION OF EMBODIMENTS

Figure 1A:
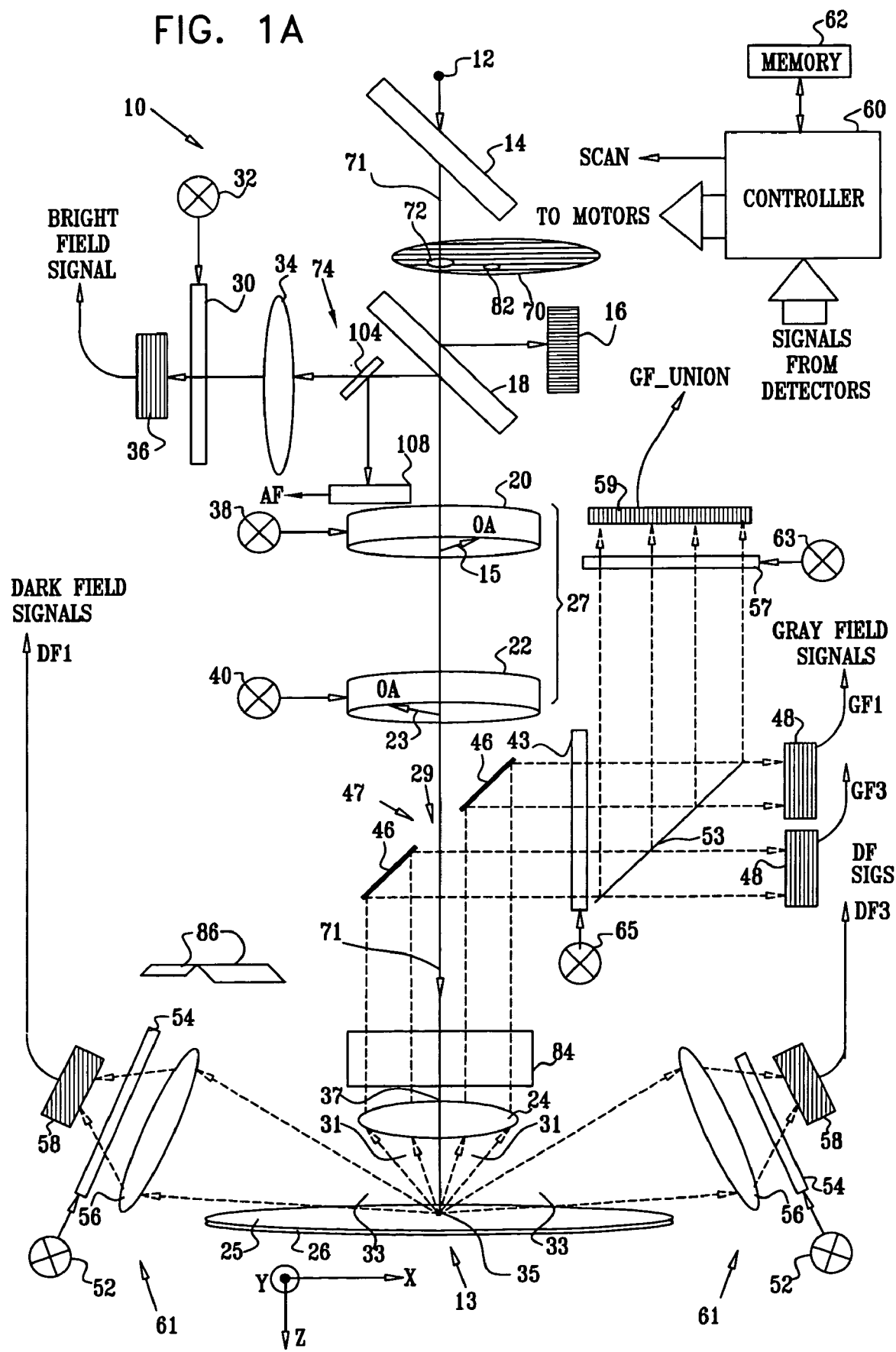
FIGS. 1A and 1B are schematic illustrations of different modes of operation of an optical inspection apparatus, according to an embodiment of the present invention.
Figure 1B:
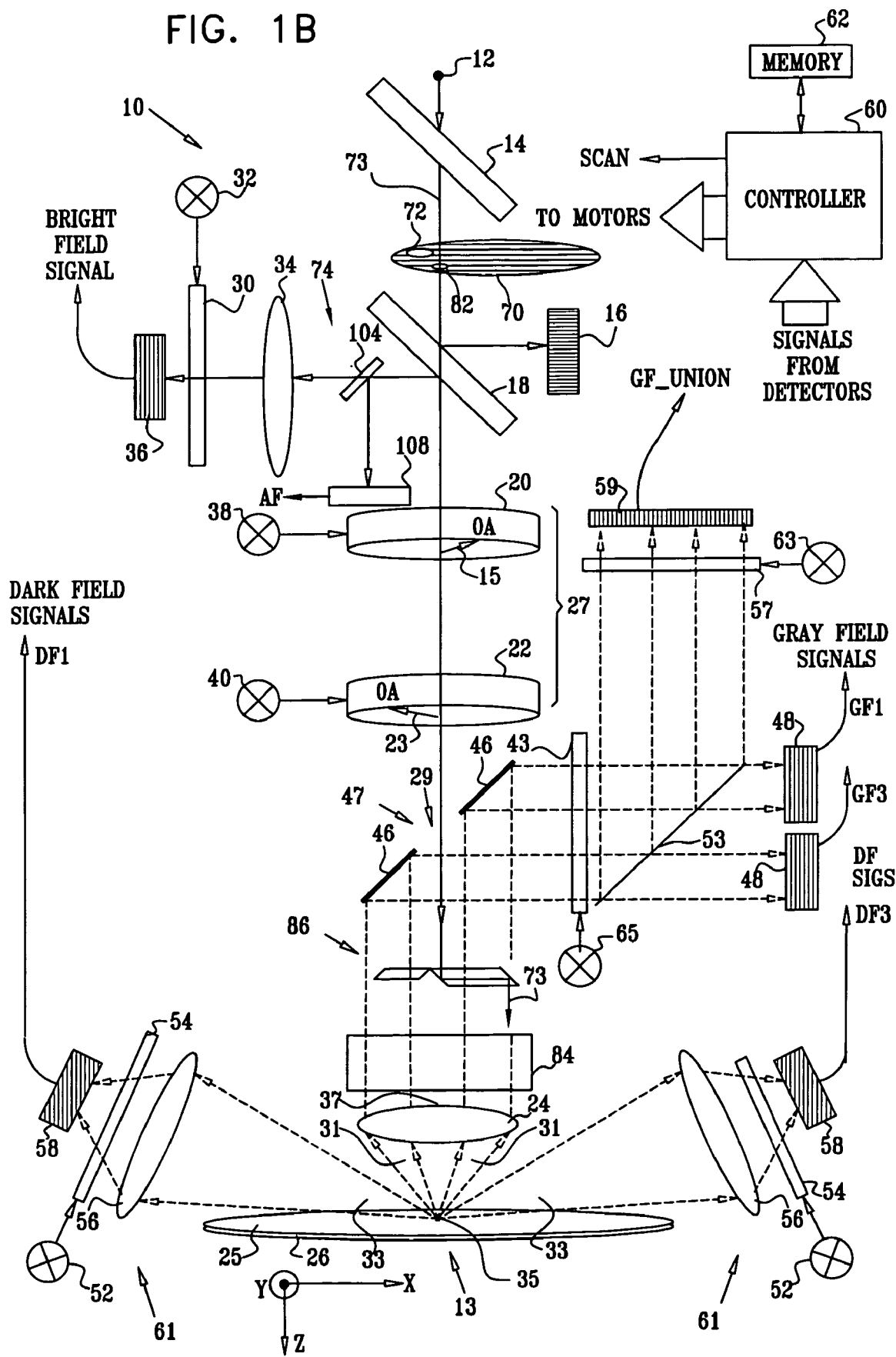

Reference is now made to FIGS. 1A and 1B, which are schematic illustrations of different modes of operation of an optical inspection apparatus 10, according to an embodiment of the present invention. FIG. 1A illustrates a first irradiation mode, hereinbelow termed a normal irradiation mode or a normal mode, wherein the apparatus irradiates a wafer 26 normally; FIG. 1B illustrates a second mode, hereinbelow termed an oblique irradiation mode or an oblique mode, wherein the wafer is irradiated obliquely. Apparatus 10 comprises a source 12, typically a laser source, which is adapted to generate a radiation beam that is focused to a spot 13 on a surface 25 of wafer 26. Apparatus 10 typically uses an auto-focus system 74 that generates a substantially similar auto-focus (AF) signal in both normal and oblique irradiation modes. Auto-focus system 74 consists of a beam splitter 104 and an auto-focus camera 108. A number of such auto-focus systems are known in the art, any suitable one of which may be used in embodiments of the present invention. An auto-focus system which may be advantageously used is described in more detail below.

U.S. patent application Ser. No. 10/903,125, titled "Determination of Irradiation Parameters for Inspection of a Surface," is assigned to the assignee of the present invention and is incorporated herein by reference. application Ser. No. 10/903,125 includes a description of elements similar to those comprised in the present application.

Apparatus 10 thus acts as an irradiation system that is able to irradiate surface 25 normally or obliquely, and that may use the same auto-focus system in both modes of irradiation. In an embodiment of the present invention, source 12 comprises a solid state diode laser generating continuous radiation at 532 nm. Unless otherwise stated herein, surface 25 is assumed to lie in an x-y plane, where an x-axis is in the plane of the paper, and a y-axis is out of the plane of the paper. Thus, in the normal irradiation mode, a path of radiation from source 12 to spot 13 is generally parallel to a z-axis, i.e., is typically incident normal to surface 25.

Apparatus 10 is used to inspect surface 25, by having spot 13 traverse the surface of the wafer. Methods for scanning spot 13 across surface 25 are known in the art. Typically the methods incorporate devices, such as acousto-optic modulators, which may be coupled to move the spot, the wafer, or both, in a controlled manner. The scan devices are controlled by a controller 60, which also controls the operation of apparatus 10. For clarity, devices for scanning spot 13 across surface 25 are omitted from FIGS. 1A and 1B.

To produce spot 13, radiation from source 12 is passed through a linear polarizer 14, which typically has an extinction ratio better than 200:1 and a transmission better than 98% for the transmitted linearly polarized radiation it produces. Polarizer 14 may advantageously be implemented from a glass plate set at the Brewster angle for the glass. Polarizer 14 outputs linearly polarized radiation having a polarization direction in the x-y plane, the polarization direction hereinbelow, unless otherwise stated, being assumed to be parallel to the x-axis.

The beam from polarizer 14 passes through a spot size controller wheel 70, which selects a size of the beam to be used, according to the mode of operation of apparatus 10. In the normal mode illustrated in FIG. 1A, controller 60 rotates wheel 70 so that the beam passes through a normal mode aperture 72 having a normal mode diameter, assumed herein by way of example to be approximately 10 mm. Thus, in the normal mode, a beam 71 having a diameter of approximately 10 mm exits aperture 72.

In the oblique mode illustrated in FIG. 1B, the controller rotates wheel 70 so that the beam passes through an oblique mode aperture 82 having a reduced diameter compared to the diameter of the normal mode beam. By way of example, oblique mode aperture 82 is assumed herein to have an approximate diameter of 7 mm. Thus, in the oblique mode, a beam 73 having a diameter of approximately 7 mm exits aperture 82.

Linearly polarized radiation beam 71 or 73 passes through a non-polarizing beam splitter 18, which typically reflects approximately 20% of the incident radiation to a beam dump 16, and transmits approximately 80% of the incident radiation as linearly polarized radiation to a quarter-wave plate 20. The inventors have found that the 80/20 transmission/reflection ratio for beam splitter 18 provides a satisfactory compromise between reflected radiation requirements of auto-focus system 74 and preference for maximum irradiation power on the wafer. It will be appreciated, however, that any other suitable transmission/reflection ratio may be used. Plate 20 is oriented so that its mechanical axis of symmetry, normal to the plane of the plate, is typically tilted at about 5° to the z-axis, to prevent stray reflections interfering with the operation of apparatus 10. The plate is coupled to a motor 38 that is controlled by controller 60, so that the motor is able to orient the plate in a controlled manner about its axis.

An optic axis 15 of plate 20 lies in the plane of the plate. Depending on the angle made by optic axis 15 with the polarization direction—the x-axis—of the incoming radiation, and assuming the angle to be non-zero, motor 38 may set the radiation exiting from the plate to be left- or right-circularly or elliptically polarized. If the angle made by optic axis 15 with the polarization direction is zero, then the radiation exiting plate 20 is linearly polarized along the x-axis.

The radiation exiting from plate 20 is transmitted to a half-wave plate 22, oriented with its mechanical axis, normal to the plane of the plate, typically tilted at about 5° to the z-axis to neutralize the effect of stray reflections. Plate 22 is coupled to a motor 40 that is controlled by controller 60 and that is able to orient the plate about its axis. An optic axis 23 of plate 22 lies in the plane of the plate. Half-wave plate 22 acts on radiation incident on the plate according to the type of polarization of the incident radiation, and according to the angle made by the direction of polarization of the incident radiation with optic axis 23. If the incident radiation is linearly polarized, plate 22 rotates the direction of polarization by 2θ, where θ is the angle between the plate's optic axis and the incident radiation's direction of polarization. If the incident radiation is elliptically polarized, plate 22 rotates the axes of the ellipse by 2θ.

The effective angle of polarization (θ) and ellipticity e of the radiation exiting the combination of plates 20 and 22 are given by equations (1):

$$\theta = 2\varphi_{\frac{\lambda}{2}} - \varphi_{\frac{\lambda}{4}} \qquad (1)$$

$$e = \begin{cases} \left|\tan(\varphi_{\frac{\lambda}{4}})\right| & 0 \le \varphi_{\frac{\lambda}{4}} < 45 \\ \left|\tan(90 - \varphi_{\frac{\lambda}{4}})\right| & 45 \le \varphi_{\frac{\lambda}{4}} < 90 \end{cases}$$

where $$\varphi_{\frac{\lambda}{4}} \text{ and } \varphi_{\frac{\lambda}{2}}$$

are the respective angles between the half-wave plate and quarter-wave plate fast axes and the incoming polarization orientation.

It will be appreciated that the combination of rotatable quarter-wave plate 20 and rotatable half-wave plate 22 gives complete control over the type of polarization of radiation transmitted from the half-wave plate, given incident linearly polarized radiation. The combination is also referred to hereinbelow as polarization controlling mechanism 27. It will also be appreciated that mechanism 27 acts as an adjustable polarizer between source 12 and surface 25. It will further be appreciated that while the description of mechanism 27 refers to rotation of half and quarter wave plates, electro-optic materials or other electrically active retarders may be used in place of plates 20 and 22 to provide the same continuously variable polarization as is provided by mechanism 27. Those skilled in the art will appreciate that mechanism 27, and any other system used to generate continuously variable polarization, has to meet certain system constraints, such as ability to withstand high radiation power densities generated by the irradiating source.

Radiation from plate 22 passes through a hole 47 in a mirror 46 oriented at 45° to the z-axis. Hole 47 is typically in the form of an ellipse that subtends, at the x-y plane, a circle approximately equal in diameter to the normal mode beam diameter, i.e., 10 mm.

In the normal mode of operation, after traversing hole 47, beam 71 passes through a rotatable turret 84 which incorporates a number of different lenses. Controller 60 operates the turret and is able to select which lenses in the turret are in the path of beam 71 after it has passed through hole 47. The selected lenses, together with an objective component 24, allow the controller to set different numerical apertures (NAs), corresponding to different magnifications, for a beam focused to spot 13 on surface 25, thus irradiating a region 35 of the surface with respective cones of different half-angles, the axis of the cones being normal to surface 25. Except where otherwise stated, component 24 is hereinbelow assumed by way of example to comprise a converging lens, and is also referred to below as objective 24. Herein, by way of example, it is assumed that controller 60 may rotate turret 84 to one of a number of positions, each generating a different magnification at surface 25, one of the magnifications being approximately 4× and another approximately 5×. In the normal mode of operation, objective 24 conveys beam 71 to region 35 via a central region 37 of the objective. It will be understood that the radiation focused on region 35 has substantially the same polarization as that output by polarization controlling mechanism 27.

In the oblique mode of operation, controller 60 inserts a beam diverter 86 into the path of beam 73 after hole 47, and rotates turret 84 to the approximately 4× or the approximately 5× magnification position. The diverter is positioned between mirror 46 and turret 84, and is typically inserted into its position, illustrated in FIG. 1B, by controller 60 operating a pneumatic arm to which the diverter is coupled. (In the normal mode of operation, controller 60 operates the pneumatic arm to remove diverter 86 from the beam path, as is illustrated in FIG. 1A.) For clarity, the pneumatic arm moving diverter 86 is not shown in FIGS. 1A and 1B; it will also be appreciated that any other system known in the art may be used to position diverter 86 in and out of the beam path, and that all such systems are assumed to be comprised within the scope of the present invention.

Figure 2:
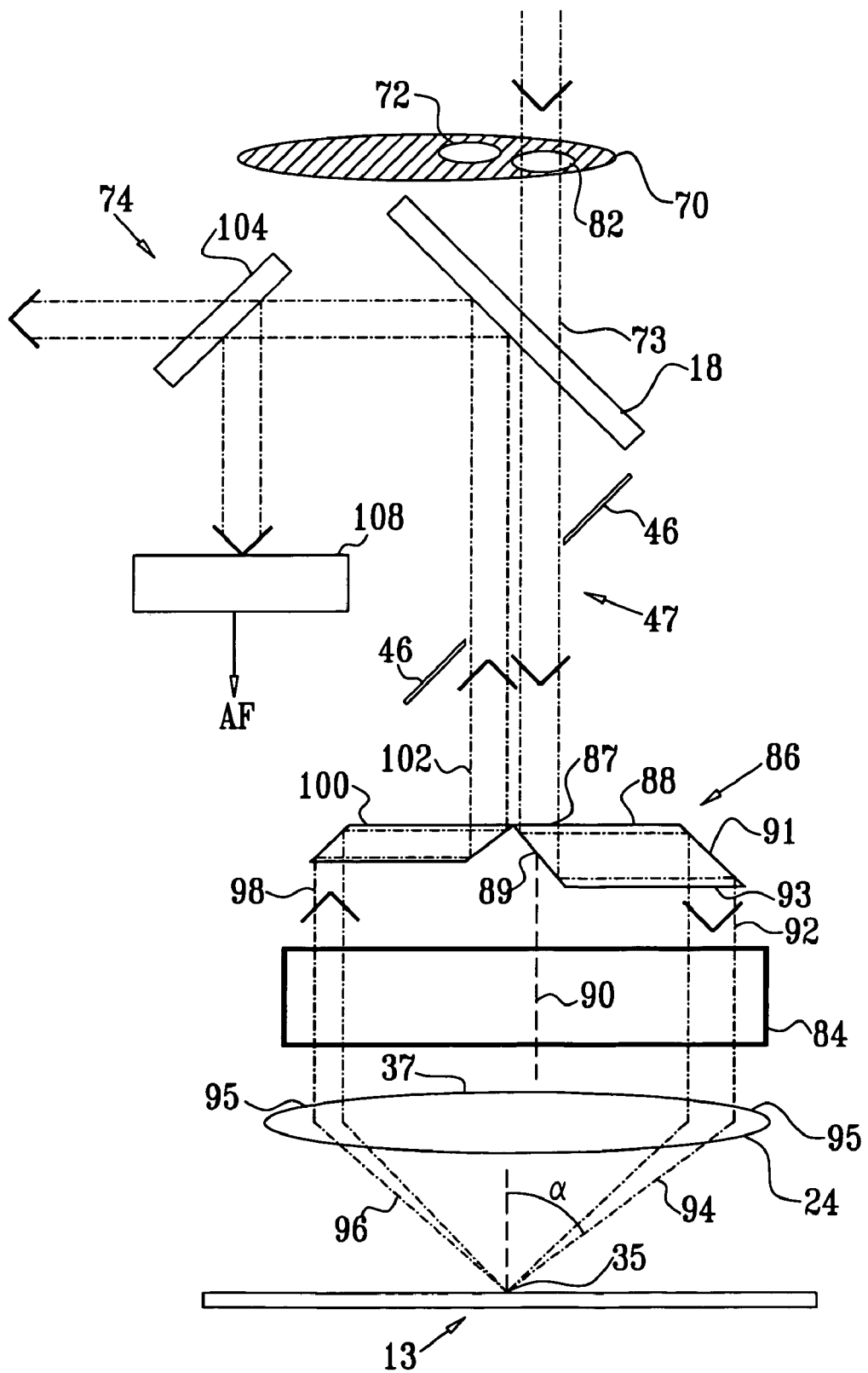
FIG. 2 illustrates the operation and construction of a beam diverter in the apparatus of FIGS. 1A and 1B, according to an embodiment of the present invention.

FIG. 2 illustrates the operation and construction of diverter 86 in apparatus 10, according to an embodiment of the present invention. For clarity, in FIG. 2 some elements of apparatus 10 have been omitted. Diverter 86 comprises a first periscope 88, which acts to divert incoming beam 73 that is produced by aperture 82 and that passes through hole 47. In the specification and in the claims, a periscope is to be understood as at least one optical element which transversely diverts a radiation beam from an initial path to a substantially parallel path in the same direction. In a disclosed embodiment of the present invention, periscope 88 is configured as a single monolithic element, typically comprising parallel reflecting facets 89 and 91, the facets typically being totally internally reflecting facets, and parallel entrance and exit facets 87 and 93. Periscope 88 diverts incoming beam 73 from its original path parallel to the z-axis, indicated in FIG. 2 by a broken line 90, to a new translated beam path 92 also parallel to the z-axis. Typically, the distance between the original path and new beam path 92 is of the order of 20 mm; by way of example the distance is herein assumed to be approximately 22 mm.

The lenses in turret 84 act as relays, conveying the beam to a peripheral region 95 of objective 24 and the objective then diverts the beam from its path 92 to a converging tilted beam 94, and focuses the tilted beam to spot 13 in region 35. Region 35 is thus irradiated obliquely. If turret 84 is set to its 4× position, tilted beam 94 irradiates region 35 at an angle α from the normal to surface 25 approximately equal to 22°; if the turret is set to its 5× position, α is approximately equal to 35°.

Tilted beam 94 is specularly reflected from region 35, at angle α, to a diverging reflected beam 96, which is converted at peripheral region 95 of objective 24, and by the lenses in turret 84, to a substantially collimated beam 98 parallel to the z-axis. A second periscope 100 comprised in diverter 86 translates beam 98 to a return collimated beam 102 which passes through hole 47, via plates 22 and 20 (FIGS. 1A and 1B) to beam splitter 18. Beam splitter 18 reflects approximately 20% of the radiation incident on the beam splitter, to beam splitter 104.

As described above, diverter 86 comprises two periscopes, which each translate an initial path of an incoming beam to a subsequent path. The translations provided by each periscope are approximately equal.

Dimensions of beams 73 and 102, and corresponding dimensions of periscopes 88 and 100, are chosen so that both beams 73 and 102 pass through hole 47. Thus, for the exemplary diameter of approximately 7 mm for beam 73, periscope 100 may be configured to form beam 102 with an approximate diameter of 3 mm. The inventors have found that this ratio of diameters provides good irradiation of surface 25 and sufficient return radiation for a bright field channel signal and auto-focus system 74, described below. Without undue experimentation, those skilled in the art will be able to determine other suitable values for dimensions of beams 73 and 102, including forming those beams to have non-circular cross-sections, the beams being able to traverse hole 47. All such dimensions and cross-sections are assumed to be comprised within the scope of the present invention. For example, one or both beams 73 and 102 may have cross-sections in the form of segments of a circle. In the disclosed embodiment referred to above, periscope 100 is configured to be one element having generally the same shape as periscope 88.

Typically, diverter 86 is configured so as not to alter the plane of polarization of beams traversing the diverter.

In both the oblique and normal modes of operation, splitter 104 reflects approximately 10% of the radiation incident on it to auto-focus camera 108, which generates an auto-focus (AF) signal that controller 60 uses to maintain spot 13 in focus by any suitable auto-focus method known in the art. For example, controller 60 may translate wafer 26 parallel to the z-axis; alternatively or additionally, controller may alter the position of diverter 86 and/or of turret 84.

In an embodiment of the present invention, auto-focus system 74 is generally similar to the system described in U.S. Pat. No. 6,124,924 to Feldman et al. In the normal irradiation mode, system 74 typically uses a double slit system, as described by Feldman et al., to generate the AF signal. In the oblique irradiation mode, typically one slit is imaged, and the image's misalignment from the in-focus position defined by the double slit system is used to generate the AF signal. It will be appreciated that in this mode, the oblique irradiation through peripheral region 95 enhances the operation of system 74.

Returning to FIGS. 1A and 1B, in both normal and oblique mode operation, splitter 104 transmits approximately 50% of the radiation incident on it, via focusing optics 34, to a bright field analyzer 30, the orientation of which is controlled via controller 60 by a motor 32. Analyzer 30, and other analyzers referred to herein, act as adjustable polarizers to filter and linearly polarize incident radiation, as is known in the art. The radiation is focused onto a bright field detector 36, and the output from detector 36 is transferred as a bright field channel signal to controller 60 for analysis, as described in more detail below.

In normal mode operation, beam 71 is specularly reflected from region 35, and follows a return path via central region 37 of objective 24 and the lenses of turret 84, through hole 47. From hole 47 the specularly reflected beam returns on a path substantially as described above for beam 102, providing an auto-focus and a bright field channel signal.

Apparatus 10 divides radiation radiating from region 35 into two or more fields. In both normal and oblique modes of operation, a first bright field 29 comprises radiation that is substantially specularly reflected from region 35, i.e., that traverses hole 47 in a return direction. It will be understood that specularly reflected radiation from region 35 arriving at analyzer 30 is, to a first approximation, linearly polarized in a direction depending on the orientation of quarter-wave plate 20. Thus, analyzer 30 may be oriented to filter out substantially all the specularly reflected radiation from region 35.

In the normal and oblique modes of operation, a near normal field 31, also herein termed a gray field, comprises radiation that is scattered from region 35 at angles between more than approximately 2° and less than approximately 45°, the angles being measured with respect to the normal to surface 25, and defining a solid angle that field 31 subtends. Radiation in gray field 31 is collimated by objective 24 and is then reflected from mirror 46.

The radiation reflected from mirror 46 passes through a first gray field analyzer 43 to an approximately 50/50 non-polarizing beam-splitter 53. Analyzer 43 is driven by a motor 65. The transmitted radiation from beam-splitter 53 is directed to four substantially similar gray field detectors 48 (for clarity only two are shown in FIGS. 1A and 1B), each detector 48 receiving radiation from approximately one quarter of field 31. The reflected radiation from beam-splitter 53 is directed via a second gray field analyzer 57 to a second gray field detector 59. Analyzer 57 is driven by a motor 63. For clarity, collimation and focusing optics between mirror 46 and detectors 48 and 59 are not shown in FIGS. 1A and 1B.

Typically, in the normal mode of apparatus 10, either analyzer 57 or analyzer 43 is positioned as described above. In a first configuration of apparatus 10, analyzer 43 is in position (so that analyzer 57 is not in position), and all five gray field detectors receive the same type of polarized radiation. In a second configuration of apparatus 10, analyzer 57 is in position (so that analyzer 43 is not in position), and only detector 59 receives polarized radiation. The output signals of detectors 48 are herein termed GF1, GF2, GF3, and GF4, and the output signal of detector 59 is herein termed GF_UNION. In one disclosed embodiment, controller 60 receives GF1, GF2, GF3, GF4, and GF_UNION as five gray field channels in the normal mode. Typically, in the oblique mode, apparatus 10 is configured to operate in the first configuration, and generates gray field channels GF1, GF2, GF3, and GF4, corresponding to forward, side, and backward scattered signals from region 35. In a further disclosed embodiment of the present invention, in the oblique mode controller 60 receives two of gray channel signal GF1, GF2, GF3, and GF4, corresponding to forward-scattered gray field signals.

In both the oblique and the normal modes of operation, a far field 33, also herein termed a dark field, comprises radiation that is scattered from region 35 at angles to surface 25 that are between approximately 5° and approximately 37°, the angles defining a solid angle that field 33 subtends. The dark field radiation transmits via focusing optics 56 and through one or more dark field analyzers 54, each analyzer having an orientation set by a respective motor 52, under the control of controller 60. The dark field radiation is focused to a respective dark field detector 58. The output from each detector 58 is transferred to controller 60. Each motor 52, polarizer 54, dark field optics 56 and detector 58 is herein collectively termed dark field detection system 61. For clarity, FIGS. 1A and 1B only show two dark field detection systems 61. Typically, apparatus 10 comprises more than one system 61, and is herein assumed by way of example to comprise four dark field detection systems 61, each of the systems being disposed symmetrically with respect to region 35, typically in azimuth directions corresponding to the four gray field channels. Thus, each system 61 receives scattered radiation from a portion of the dark field. The output signals of detectors 58 are termed DF1, DF2, DF3, and DF4 and are available to controller 60 as four dark field channels.

In the normal mode of operation, the four dark fields 33 are substantially symmetrically disposed about beam 71. In the oblique mode of operation, the four dark fields are asymmetrically disposed about beam 94 (FIG. 2), and receive forward-scattered, back-scattered and side-scattered radiation from region 35. It will be appreciated that in both the normal and the oblique modes controller 60 may choose between signals DF1, DF2, DF3, and DF4 to optimize measurements used in apparatus 10. In the further disclosed embodiment of the present invention referred to above, in the oblique mode controller 60 may only use the signals corresponding to back-scattered radiation to improve signal to noise measurements of scattered radiation.

Controller 60 acts as a central processing unit for apparatus 10, providing signals to set motors 32, 38, 40, 63, 65, and 52 as it scans spot 13 over surface 25. Controller 60 typically comprises one or more analog-digital (A/D) converters which convert analog signals generated by detectors 36, 48, 59, and 58, and/or sums from the detectors as described above, to digital values, which are in turn stored in a memory 62 coupled to the controller.

As stated above, apparatus 10 may be used to scan surface 25 so as to locate defects on the surface. A defect typically comprises, but is not limited to, an extraneous particle on surface 25, a contaminant on the surface, a short between conductors on the surface, and a break in a conductor. The defect typically causes a difference in polarization characteristics of radiation radiating from the region of the defect, compared to the polarization characteristics of radiation radiating from the same region if no defect is present. The polarization characteristics of radiation from such a "non-defect region" are typically a function of the polarization characteristics of the irradiating radiation and of the region itself. For example, if the region comprises a patterned region made up of relatively closely spaced parallel conductors, the parallel conductors influence the polarization characteristics of the radiation from the region. Other factors which influence the polarization characteristics of radiation from the region will be apparent to those skilled in the art.

U.S. patent application Ser. No. 10/903,125, referenced above, describes apparatus for detecting defects on a surface of a wafer. The application also describes a process to determine settings of elements of the apparatus to be used when regions of the surface are irradiated. The application further describes an exemplary process for examination of the wafer after the settings have been determined. Those skilled in the art will be able to use the application, mutatis mutandis, in order to determine settings of plates 20 and 22, and analyzers 30, 43, 54, and 57 of the present invention, for both the normal and oblique modes of operation of apparatus 10, as well as to apply the settings to determine defects on wafer 26.

While the description hereinabove has assumed that irradiation of surface 25 uses generally transparent optic elements, it will be appreciated that the principles of the present invention are not limited to use of such elements. For example, as will be apparent to those skilled in the art, objective component 24 may be configured to comprise at least a partially reflecting mirror. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus for inspection of a surface, comprising:
   an objective component having central and peripheral regions, which is adapted to focus an input beam through the central region in a normal direction onto the surface, and to focus the input beam through the peripheral region in an oblique direction onto the surface;
   a first periscope which is adapted to selectively divert the input beam so as to pass through the peripheral region of the objective component; and
   a second periscope which is adapted to selectively capture radiation reflected from the surface in the oblique direction after passage of the reflected radiation through the peripheral region of the objective component, wherein
   at least one of the first and second periscopes is configured as a single monolithic element.

2. The apparatus according to claim 1 wherein the single monolithic element comprises an entrance and an exit facet, and one or more reflecting facets, the facets acting in combination to divert radiation entering the single monolithic element.

3. Apparatus for inspection of a surface, comprising:
   an objective component having central and peripheral regions, which is adapted to focus an input beam through the central region in a normal direction onto the surface, and to focus the input beam through the peripheral region in an oblique direction onto the surface;
   a first periscope which is adapted to selectively divert the input beam so as to pass through the peripheral region of the objective component; and
   a second periscope which is adapted to selectively capture radiation reflected from the surface in the oblique direction after passage of the reflected radiation through the peripheral region of the objective component, wherein the first and the second periscopes are fixedly coupled together.

4. Apparatus for inspection of a surface, comprising: an objective component having central and peripheral regions, which is adapted to focus an input beam through the central region in a normal direction onto the surface, and to focus the input beam through the peripheral region in an oblique direction onto the surface; a first periscope which is adapted to selectively divert the input beam so as to pass through the peripheral region of the objective component; and a second periscope which is adapted to selectively capture radiation reflected from the surface in the oblique direction after passage of the reflected radiation through the peripheral region of the objective component, wherein the first and the second periscopes are positionable so that, in a normal irradiation mode, the input beam is directed towards the central region of the objective component and so that, in an oblique irradiation mode, the input beam is directed towards the peripheral region of the objective component.

5. The apparatus according to claim 4, wherein in the normal irradiation mode the input beam has a normal-mode diameter, and wherein in the oblique irradiation mode the input beam has an oblique-mode diameter, and wherein in the oblique irradiation mode the reflected radiation is formed into a reflected beam having a reflected diameter approximately equal to a difference between the normal-mode and the oblique-mode diameters.

6. The apparatus according to claim 4, wherein in the oblique irradiation mode the reflected radiation is formed into a reflected beam contiguous with the input beam.

7. A method for inspecting a surface, comprising:
   focusing, through an objective component having central and peripheral regions, an input beam through the central region in a normal direction onto the surface, and through the peripheral region in an oblique direction onto the surface;
   selectively diverting, with a first periscope, the input beam to pass through the peripheral region of the objective component;
   selectively capturing, with a second periscope, radiation reflected from the surface in the oblique direction after passage of the reflected radiation through the peripheral region of the objective component; and
   detecting defects on the surface, said defects being manifested by polarization characteristics of the captured radiation, wherein at least one of the first and second periscopes is configured as a single monolithic element.

8. The method according to claim 7 wherein the single monolithic element comprises an entrance and an exit facet, and one or more reflecting facets, the facets acting in combination to divert radiation entering the single monolithic element.

9. A method for inspecting a surface, comprising:

focusing, through an objective component having central and peripheral regions, an input beam through the central region in a normal direction onto the surface, and through the peripheral region in an oblique direction onto the surface;

selectively diverting, with a first periscope, the input beam to pass through the peripheral region of the objective component;

selectively capturing, with a second periscope, radiation reflected from the surface in the oblique direction after passage of the reflected radiation through the peripheral region of the objective component; and fixedly coupling the first and the second periscopes together; and detecting defects on the surface, said defects being manifested by polarization characteristics of the captured radiation.

10. A method for inspecting a surface, comprising:

focusing, through an objective component having central and peripheral regions, an input beam through the central region in a normal direction onto the surface, and through the peripheral region in an oblique direction onto the surface;

selectively diverting, with a first periscope, the input beam to pass through the peripheral region of the objective component;

selectively capturing, with a second periscope, radiation reflected from the surface in the oblique direction after passage of the reflected radiation through the peripheral region of the objective component; and positioning the first and the second periscopes so that, in a normal irradiation mode, the input beam is directed towards the central region of the objective component and so that, in an oblique irradiation mode, the input beam is directed towards the peripheral region of the objective component; and detecting defects on the surface, said defects being manifested by polarization characteristics of the captured radiation.

11. The method according to claim 10, wherein in the normal irradiation mode the input beam has a normal-mode diameter, and wherein in the oblique irradiation mode the input beam has an oblique-mode diameter, and wherein in the oblique irradiation mode the reflected radiation is formed into a reflected beam having a reflected diameter approximately equal to a difference between the normal-mode and the oblique-mode diameters.

12. The method according to claim 10, and comprising in the oblique irradiation mode positioning the second periscope to form the reflected radiation into a reflected beam contiguous with the input beam.

* * * * *